US012728240B2

(12) United States Patent
Hakki et al.

(10) Patent No.: US 12,728,240 B2
(45) Date of Patent: Sep. 8, 2026

(54) DOUBLE WALL BALLOON CATHETER SYSTEM

(71) Applicants: A-Hamid Hakki, Dunedin, FL (US); A-Hadi Hakki, Largo, FL (US); Tariq Said Hakky, Atlanta, GA (US)

(72) Inventors: A-Hamid Hakki, Dunedin, FL (US); A-Hadi Hakki, Largo, FL (US); Tariq Said Hakky, Atlanta, GA (US)

(*) Notice: Subject to any disclaimer, the term of this patent is extended or adjusted under 35 U.S.C. 154(b) by 49 days.

(21) Appl. No.: 18/957,230

(22) Filed: Nov. 22, 2024

(65) Prior Publication Data

US 2026/0144969 A1 May 28, 2026

(51) Int. Cl.
*A61M 25/10* (2013.01)

(52) U.S. Cl.
CPC .. *A61M 25/10184* (2013.11); *A61M 25/1011* (2013.01)

(58) Field of Classification Search
CPC .......... A61M 25/1002; A61M 25/1011; A61M 2025/1013; A61M 2025/1015; A61M 2025/105; A61M 2025/1086; A61M 2025/1095
See application file for complete search history.

(56) References Cited

U.S. PATENT DOCUMENTS 4,744,366 A * 5/1988 Jang .................... A61M 25/104 604/101.02
5,049,132 A * 9/1991 Shaffer ............. A61M 16/0456 604/101.02
5,306,250 A * 4/1994 March ............... A61M 16/0481 604/104
6,186,978 B1 * 2/2001 Samson ............. A61M 25/005 604/525
12,186,506 B2 * 1/2025 Smith ................ A61B 17/0057
2007/0016241 A1 * 1/2007 von Oepen ......... A61M 25/104 606/192
2007/0185445 A1 * 8/2007 Nahon .............. A61M 25/1011 604/96.01
2012/0253278 A1 * 10/2012 Ise .................. A61B 17/12113 606/200
2014/0364834 A1 * 12/2014 McCullough ...... A61M 25/1011 604/509
2020/0316350 A1 * 10/2020 Patel ...................... A61N 1/325

* cited by examiner

*Primary Examiner* — Theodore J Stigell
*Assistant Examiner* — Benjamin Koo
(74) *Attorney, Agent, or Firm* — Rosenberg, Klein & Lee

(57) ABSTRACT

An open balloon indwelling catheter for drainage from, irrigation to, and retention within a patient's body cavity. The indwelling catheter has a hollow tube catheter member. A double walled balloon having an inner wall and an outer wall is attached to a sidewall of the hollow tube catheter member. The hollow tube catheter member has catheter orifices formed through the sidewall in an area covered by the double walled balloon. Balloon orifices are formed through the double walled balloon for passage of fluid from the body cavity. An inflation passageway is created between the inner and outer walls of the ballon for inflating the double walled balloon. When the double walled balloon is inflated the bodily fluid is transmitted from the body cavity through the balloon orifices and the catheter orifices to a catheter lumen for disposal.

15 Claims, 5 Drawing Sheets

DOUBLE WALL BALLOON CATHETER SYSTEM

FIELD OF THE INVENTION

The present invention relates to surgical devices used in medical procedures.

In particular the subject invention is directed to surgical devices inserted into a patient's body cavity for retaining the surgical device within the body cavity while simultaneously draining unwanted bodily fluids from the patient's body cavity.

Still further the subject invention relates to balloon catheter systems which are inserted into a patient's body cavity and remain in a relatively fixed location during or subsequent to a surgical procedure.

Additionally, the subject invention is directed to a balloon catheter system which includes a balloon construction which allows for retention and simultaneous draining of unwanted fluids from the patients body after insertion into the patients body cavity.

Further the subject invention relates to a balloon catheter system which includes at least a double wall balloon construction secured to a catheter member which can be inflated to expand radially within the patient's body cavity for restraining the balloon catheter within the patients body cavity.

More in particular the subject invention is directed to a balloon catheter system having a one or more balloon orifices formed through an outer wall and an inner wall of the balloon and in fluid communication with a catheter lumen for dispensing of unwanted bodily fluids.

Further the subject invention provides for an insertion conduit which provides for a gas or fluid to be inserted into an annular insertion passageway between an outer balloon wall and an inner balloon wall while maintaining independence between unwanted fluid being drained and expansion of the balloon under pressured fluid or gas being inserted in the annular insertion passageway.

Still further, the subject invention provides for a balloon catheter system which has a mechanism for providing medicants to be inserted through the double wall balloon into the body cavity for treating a particular ailment.

More in particular, the subject invention concept provides for a double balloon catheter system which may be inserted into the bladder of a patient for restraining the balloon catheter from removal of the double wall balloon catheter system from the patient's bladder while simultaneously draining urine or other unwanted fluids from the patients body.

Still further the subject invention concept provides for a secondary double wall balloon mounted to a catheter where the secondary double wall balloon having a double wall construction has the means of providing medicant to be applied to the prostate of a patient.

BACKGROUND OF THE INVENTION

Indwelling catheters are necessary in a number of surgical procedures to remove unwanted body fluids and perhaps provide medicant to the patient's body through the indwelling catheter. In a particular field, urinary catheters are designed for insertion into the bladder of a patient and remains located therein through the duration of a particular procedure and in post-operative times. It is believed that the use of indwelling catheters dates back to the 6$^{th}$ century B.C. and is attributed to an Indian surgeon Sushruta. This described the use of urinary retention urethral structures and lithotomy. These catheters were made of a solid material generally gold, silver, iron and wood with clarified butter used as a lubricant used for insertion and removal. Improvements were developed and it is believed that around the 9$^{th}$ century Al Razi taught the use of a stylet in the lumen of a catheter aiding in the surgical procedure.

Avicenna, an Iranian scientist, provided a canon of medicine and urology enumerating a number of urinary symptoms and is generally known for the documentation and use of flexible catheters made from softened animal skins. This was further developed with the discovery of vulcanized rubber and Aguste Nelaton's rubber catheters which were flexible but firm and adaptable for insertion through the urethra of a patient.

The concept of retention of a catheter within a body cavity was developed by Frederic Foley and is commonly known as the Foley catheter which is believed to the first one-piece catheter with a self-retaining balloon. The C.R. Bard company is believed to have begun distributing Foley catheters around 1935 in catheters commonly referred to as the "Foley catheter". Such urinary catheters are seen in U.S. Pat. No. 5,137,671 and numerous patent developments relating to the "Foley catheter".

In what is termed acute/chronic surgical/medical conditions it has been found desirable to continuously drain the urine from a patient's bladder for irrigation of the bladder or for the transmission of a medicant to the patient's body.

It has been found desirable in many cases to drain the urinary bladder to measure some type of hourly urinary output which may be an indicator of kidney function in the study of the pulse rate, fluctuations in blood pressure, and cardiac monitoring.

The use of a system for draining the bladder is known to aid in the recovery in a number of patient debilitating conditions and indwelling urinary catheters in particular may be used for patient's suffering from complicated neurological diseases or patients who may be heavily sedated and unable to empty their bladder.

Additionally, in a prostate surgery, post-operative bleeding may be coming and if left unchecked may lead to formation of blood clots in the bladder itself thus, indwelling urinary catheters may be mandatory to ensure that the bladder is not filled with clotting blood and to avoid other painful conditions.

In certain post-prostate/bladder surgeries, the urinary bladder is generally continuously irrigated with fluid for preventing blood from clotting within the urinary bladder. In chronic medical/surgical conditions the urinary bladder may be drained for an extensive length of time post-operative where the patient may be debilitated and unable to urinate when the patient's medical condition prohibits any further surgical intervention.

In generally acute clinical cases, a urinary catheter is generally inserted within the bladder of a patient through the urethra. Urine may be drained from the bladder and collected in an external container commonly known as a urine bag for urine output measurements. This procedure is generally a standard procedure used in major surgeries or in intensive care unit settings.

In acute settings, the urinary catheter may be maintained within the bladder for post-operative time intervals which may range from a few hours to days or even weeks.

In clinical studies, urinary catheters may be used in a permanent manner for patients who are unable to urinate by themselves. One approach in this methodology is to introduce a urinary catheter into the bladder and in chronic cases this may be a supra-pubic catheterization where the catheter is inserted through the anterior abdominal wall of the patient. In accordance with this methodology, the urinary catheter is connected through the interior abdominal wall into the bladder and may be left in this location for extended periods of time which may in some cases extend for the life of the patient.

Balloon inflatable urinary catheter systems have developed where the catheter remains within the bladder until the catheter is to be removed. In these cases sterile fluid may be inserted into the catheter and a balloon is attached throughout a portion of the length of the catheter for expansion when the catheter is inserted into the patient's body cavity and an example would be the bladder of the patient. This aids in the retention of the indwelling catheter since once inflated, the diameter of the balloon itself is greater than the diameter of the urethra and thus allows for some retention of the balloon within the bladder of the patient.

When the surgical procedure or post-operative time interval is completed, the catheter may be removed from the bladder by draining the sterile fluid removed from the balloon through use of a syringe or some-like removal apparatus engaged with an injection port. When the balloon is deflated, the balloon surfaces are substantially adjacent to an external surface of the catheter member and the catheter can then be removed through the urethra.

PRIOR ART

The field of providing a body cavity indwelling catheter which has the capability of permitting draining of unwanted body fluids while simultaneously providing a retention device which maintains the catheter in a relatively fixed position for preventing dislodgement from within the body cavity during normal movements by a patient has been the result of extensive research and development of improved catheters.

The most widely known catheter is the foley catheter which has been use since the mid-20$^{th}$ Century. Numerous improvements have been made to the Foley Catheter with limited success. The Foley Catheter is believed to be the first or one of the first balloon catheters which relies on a balloon member to be inflated once the Foley Catheter is inserted into the body cavity of the patient and was specifically directed to draining urine from the bladder of a patient.

The Foley Catheter generally includes a single walled balloon surrounding and attached to a longitudinally extending catheter member. The Foley Catheter is inserted through the urethra into the patients bladder with the single walled balloon in a collapsed state. Once inserted into the patient's bladder a conduit formed in the wall of the longitudinally extending catheter member inflates the single wall balloon with generally sterile fluid which expands the balloon to a diameter greater than the diameter of the urethra to prevent dislodgement of the Foley Catheter from the bladder. A tip of the elongated longitudinally extending catheter member generally has a draining orifice or orifices to permit draining of urine from the bladder to a catheter lumen for dispensing purposes.

The Foley Catheter (and variations thereof) require a tip section of the longitudinally extending member to be of a significant length which can produce irritation of the bladder wall. Further the Foley Catheter requires the balloon to be filled with sterile fluid which greatly increases the weight of the Foley Catheter and causes irritation of the bladder wall due to the pressure exerted on the sensitive trigone portion of the patient's bladder. Additionally the draining of residual urine is compromised since the draining orifices are generally formed through the catheter wall in a restricted area namely the tip section of the of the longitudinally extending catheter member. In use the Foley Catheter may result in significant damage to the urethra if inadvertently the catheter is removed from the bladder while the balloon is in an inflated state.

Other prior art catheter systems for draining of bodily fluids while retaining the catheter in the bodily cavity have been developed which have limited success such as the catheter system described in the Termanini Patent #4,154,242 which does not rely on an expandable balloon.

The Termanini bladder catheter includes a longitudinally extending tubular member with a draining lumen that extends from a proximal end section to a distal end section. A plurality of longitudinal slits are formed through the tubular member wall in the distal section in a radial pattern around the tubular member. A mechanism is provided where the distal end section of the tubular member may be retracted for displacement toward the proximal end section.

This retraction of the distal end section of the tubular member (due to the slits) causes the sections of between the slits to enlarge to a diameter greater than the diameter of the urethra and constrain the Termanini catheter within the confines of the bladder.

The advantage of the Termanini catheter with respect to the Foley catheter is that the Termanini catheter dispenses with the necessary fluid filled balloon concept of the Foley catheter Thus the Termanini catheter minimizes the weight of the fluid filled balloon of the Foley catheter exering on the mucosa and the trigone area of the bladder.

However the disadvantage of the Termanini catheter and other like catheters is they have a partially open tube or mesh which may cause ingrowth of body tissue such as bladder mucosa into the expanded slits or mesh causing polypoid cystitis or papillary hyperplasia. These are finger-like projections growing out of the mucosal proliferation and may be the source hemorrhage when the catheter is manipulated or withdrawn from the bladder.

Additionally, trauma tissue which can be caused by the narrow surface area of the areas between the slits pressing on the bladder lining which provides a greater force on the surrounding tissue resulting in possible tissue trauma.

There is a long standing need for providing an improved balloon catheter system which reduces the weight of the balloon when inserted into a patient's body, reduces the trauma to a patients internal tissue, reduces possible infection when the balloon is retained in the patients body for an extended period of time, improves the draining of unwanted body fluids, and is easily removable from the patients body with a minimum amount of trauma to the patient.

SUMMARY OF THE INVENTION

A double wall balloon catheter system is provided for retention in a patients body cavity with the simultaneous ability to drain bodily fluid from the body cavity. A longitudinally extending catheter member defines a longitudinally extending catheter lumen within a wall or sidewall of the catheter member. The catheter member has at least one catheter drainage orifice or plurality of drainage orifices are formed through the catheter sidewall for accepting passage of bodily fluid into the catheter lumen for removal of the bodily fluid from the catheter system and disposal.

A double wall balloon having a series of bodily fluid drain passages is secured to an external surface of the catheter with the double wall balloon covering the drainage orifices.

The double wall balloon is formed having at least a double wall configuration defining an inner and outer balloon walls respectively. An annular balloon passageway is formed between the inner and outer balloon walls which is generally filled with a sterile aqueous solution. A longitudinally inflation conduit is formed within the catheter member for insertion of the sterile aqueous solution into the passageway for expansion of the inner and outer wall balloon members within the patient's body cavity. Unwanted bodily fluid is drained from the bodily cavity, through the balloon fluid passages to an inner region of the balloon which is in fluid communication with the catheter member lumen through the catheter member orifices into the catheter lumen for removal and disposal.

An object of the subject concept is to provide an improved catheter system which provides a minimum catheter system weight, a minimum of tissue trauma when retained within a patient's body cavity, and lessens the possibility of infection.

A further object of the subject concept is to provide a balloon having at least one double wall configuration which permits unwanted body fluid to be drained through an outer wall and inner wall of the balloon for eventual passage into a catheter member lumen for disposal of the bodily fluid.

A still further object of the subject concept is to provide a double wall balloon catheter system which includes a plurality of cathode drainage orifices formed through a catheter wall within an area which is covered by the double wall balloon for disposal of unwanted bodily fluid.

An additional object of the subject concept tis to provide a double wall balloon catheter system where a double wall balloon is expanded in a radial direction by insertion of inflation fluid within a narrow passageway formed between an inner and outer wall of a double wall balloon for minimizing the weight of the inflation fluid needed for inflation of the double wall balloon.

A further object of the subject concept is to provide a double wall balloon catheter system which includes a blunted rather short tip portion which may be substantially devoid of draining orifices or have a minimum number of orifices.

Another object of the subject concept is to provide a double wall balloon catheter system which includes an inner region of an inflated double wall balloon in fluid communication with the body cavity external to the double wall balloon catheter system and the catheter lumen for dispensing and disposal of unwanted bodily fluid.

A still further object of the invention is to provide a double wall balloon catheter system where the inflated balloon is not encumbered by sharp edges so that the walls of the cavity are not traumatized.

DESCRIPTION OF PREFERRED EMBODIMENTS

Figure 1:
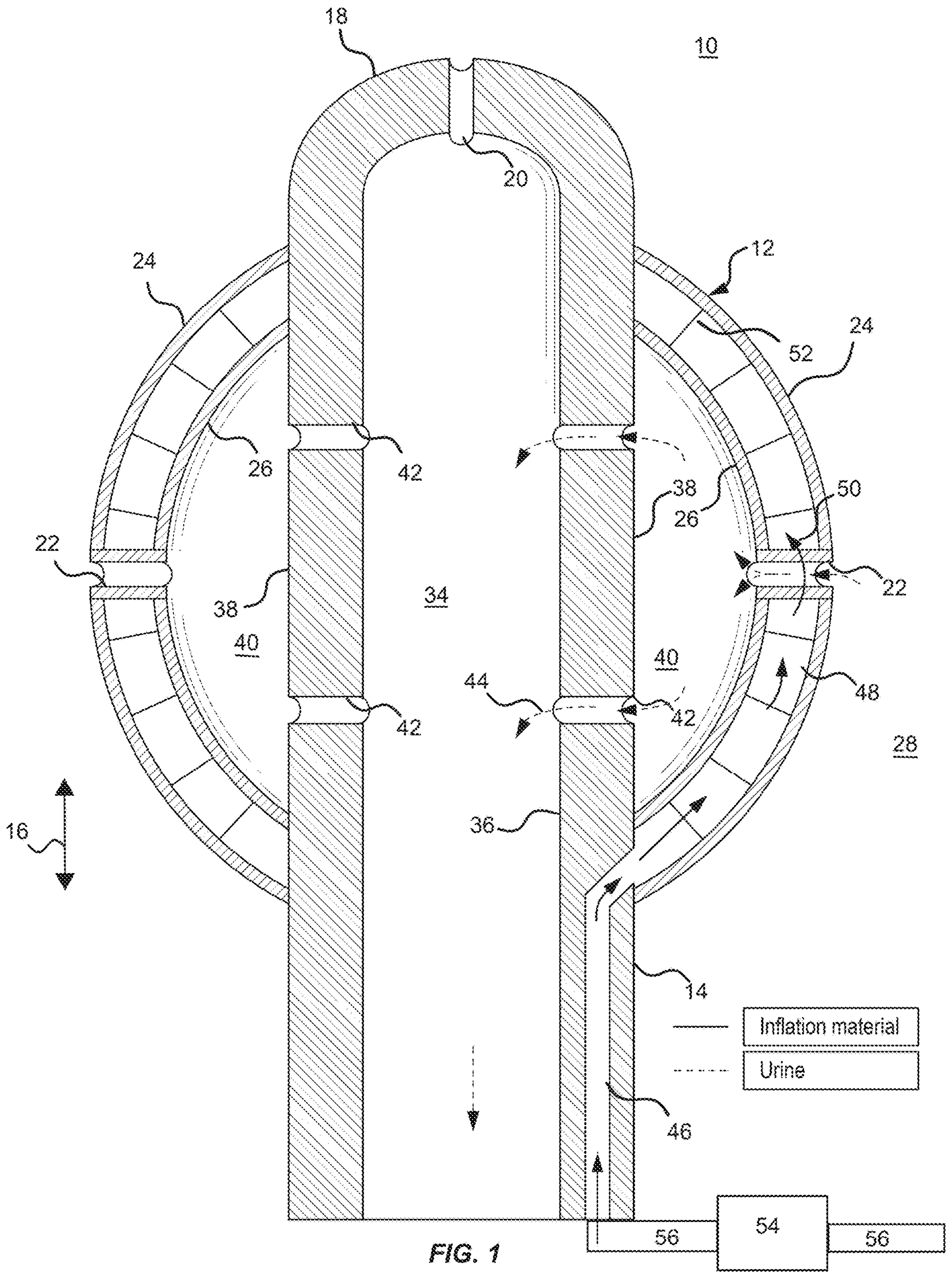
FIG. 1 is a schematic cross-sectional view of the double wall balloon catheter system showing an inner balloon wall tethered to an outer balloon wall by thread or band like members.

Referring now to FIGS. 1-4 there is shown double wall balloon catheter system 10 for insertion into a body cavity 28 of a patient. Double wall balloon catheter system 10 in particular provides for positioning double wall balloon catheter system 10 within the body 28 which for example may be the bladder of a patient. The double wall balloon catheter system 10 provides for placement, secure location and retention of double wall balloon catheter system 10 within the bladder cavity 28.

Additionally, double wall balloon catheter system 10 provides for a draining orifice 22 which permits draining from internal body or bladder cavity 28 into catheter lumen 34 in a manner to be further detailed in following paragraphs. Double wall balloon 12 may be inflated to block any inadvertent removal of catheter 14 from bladder cavity 28 while simultaneously providing drainage capabilities from bladder cavity 28 in an optimal manner.

Figure 3A:
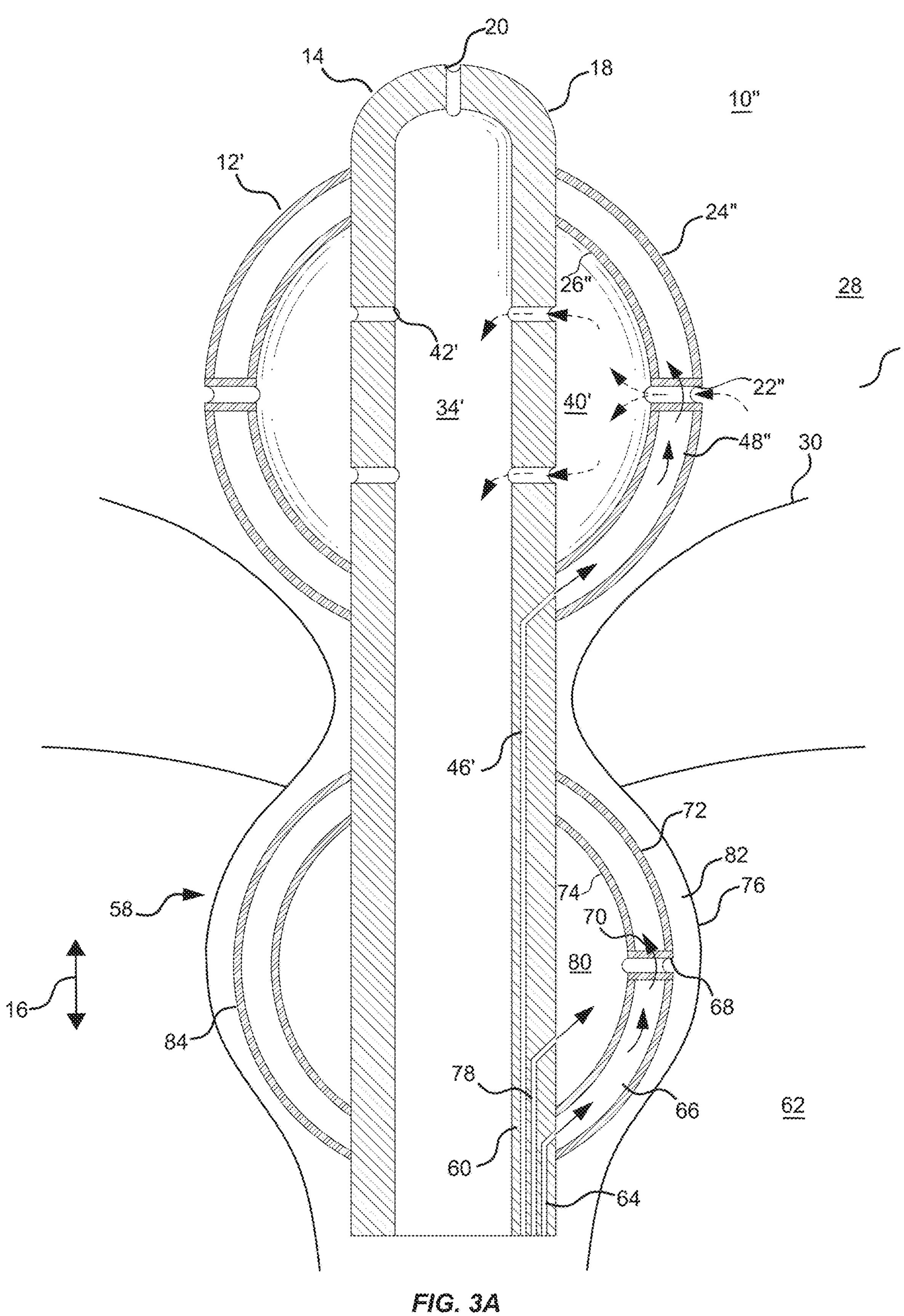
FIG. 3A is a schematic cross-sectional view of the double wall balloon catheter system which includes a first double wall balloon positioned in the bladder of a patient and a second double wall positioned in the prostate of a patient for providing medicant.
Figure 3B:
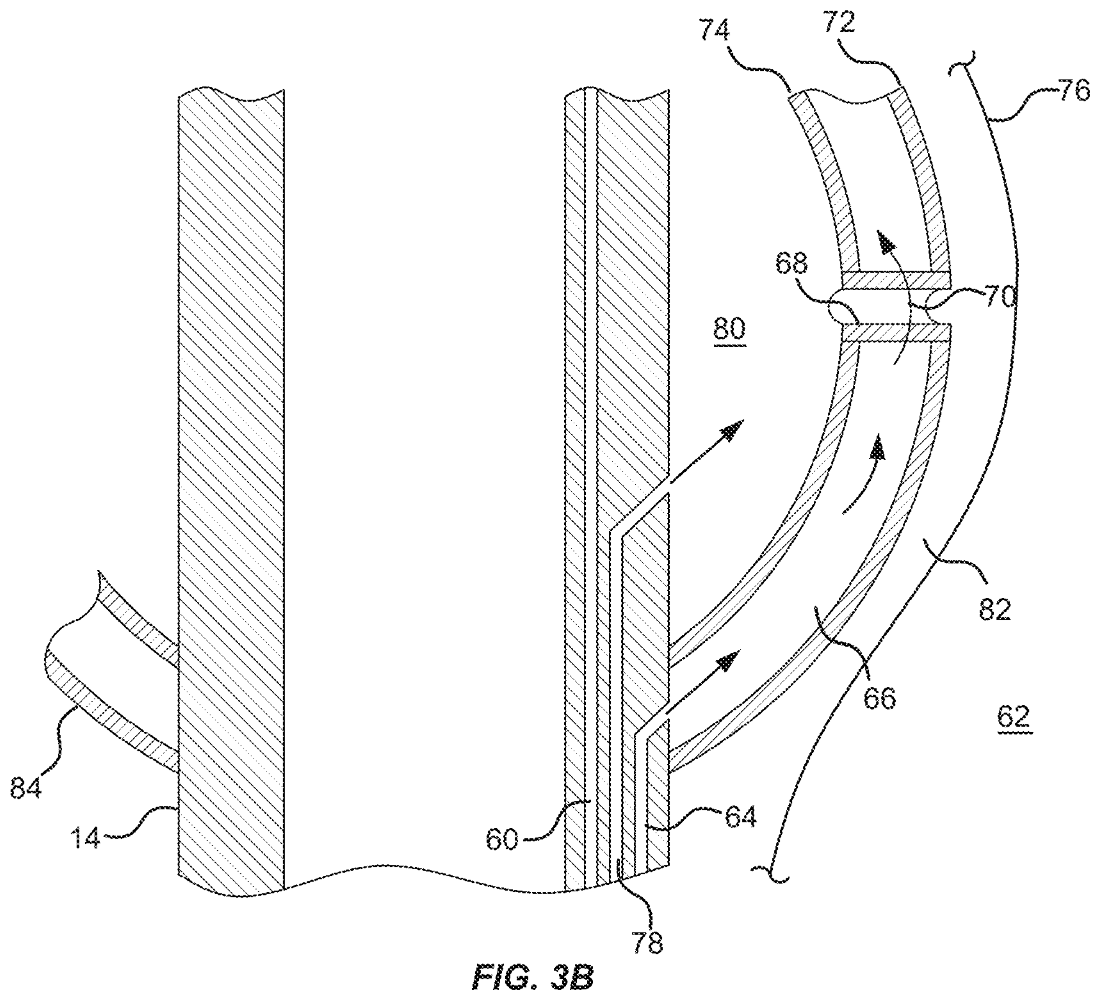
FIG. 3B is an enlarged schematic cross-sectional view of the double wall balloon catheter system showing the second double wall balloon within the prostate of a patient; and, FIG. 4 is a perspective view (not to scale) of the double wall balloon catheter system.
Figure 4:
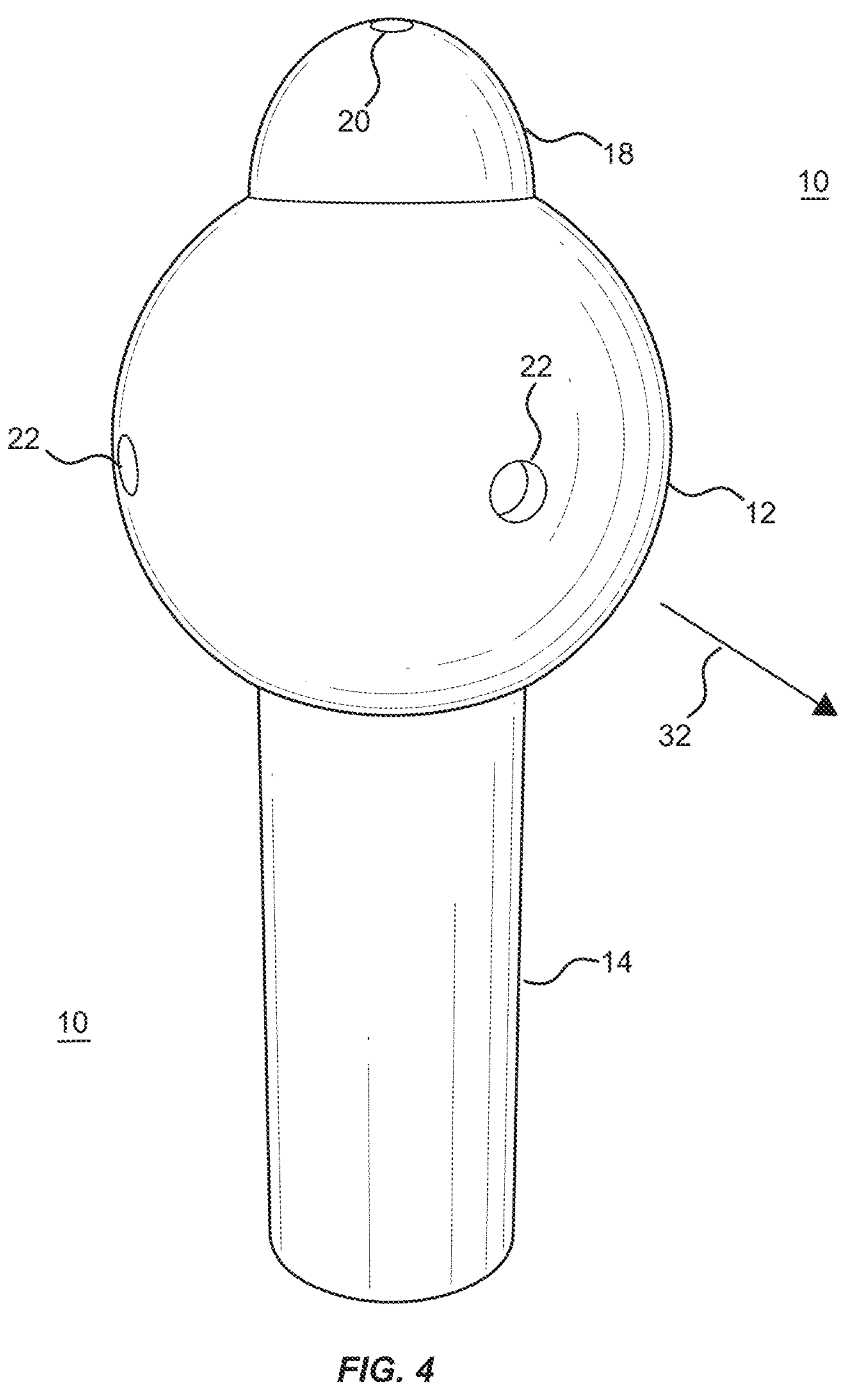

Catheter or catheter member 14 defines a diameter having a dimension which allows access into the body cavity 28. In the case of double wall balloon catheter system 10 being used in urological procedures for insertion of catheter system 10 into the bladder of a patient, the diameter of catheter member 14 must be of a dimension which will allow passage of catheter member 14 to be inserted through the urethra of the patient as depicted in FIGS. 3A-3B.

Figure 2:
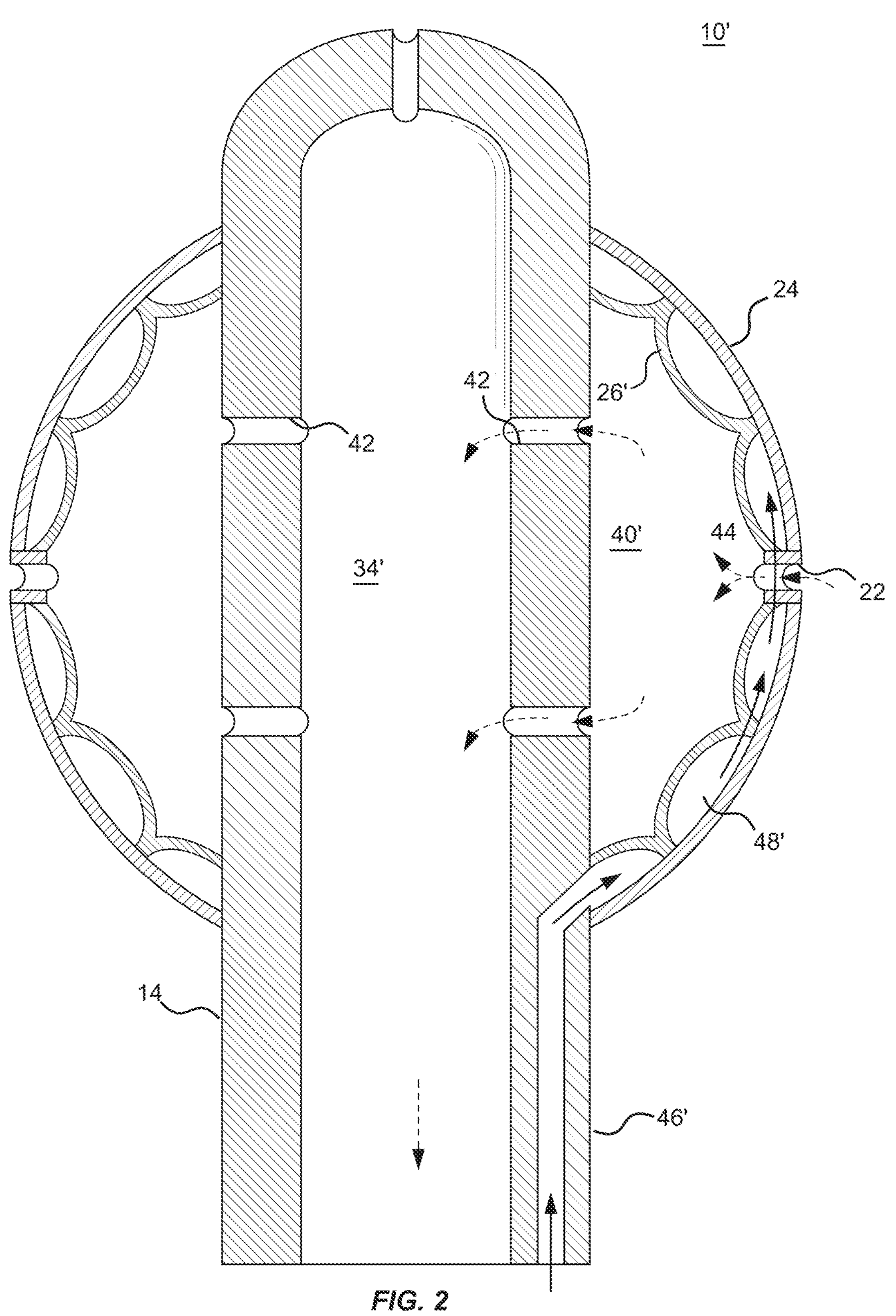
FIG. 2 is a schematic cross-sectional view of the double wall balloon catheter system showing the inner balloon wall secured to the outer balloon wall member at cusp points of the inner wall.

As seen in FIGS. 1-2, double wall balloon 12 is formed of balloon outer wall 24 and balloon inner wall 26 which are formed in one piece formation through molding, or some like technique not important to the inventive concept as herein described with the exception that the double wall balloon 12 is formed in one piece formation and has a composition acceptable for surgical procedures.

Catheter or catheter member 14 includes a catheter tip section 18 which may or may not have a drain orifice 20 (to be further described). Drain orifice 20 provides fluid communication between the catheter lumen 34 and the bladder cavity 28 to provide a drainage mechanism for unwanted bladder cavity fluids. In the case where double wall balloon bladder system 10 is inserted into the bladder of the patient, such unwanted body fluid would include urine to be disposed of through passage of the bodily urine from body cavity 28 which in this case is the bladder cavity. In this case the urine passes from the body cavity 28 through drain orifice 20 into catheter lumen 34 for disposal of the unwanted body fluid.

Catheter 14 having catheter wall 36 may be formed of a surgically acceptable and bio-compatible material such as close-cell plastic or close-cell flexible plastic or some like composition not important to the inventive concept with the exception that the composition have some flexibility but must have sufficient stiffness to permit insertion. Such compositions are well known and are commercially available.

Double wall balloon 12 (to be discussed further) is formed of sheets of a bio-compatible composition which are secured to catheter member 14 on an outer surface of the catheter sidewall. When double wall balloon 12 is in a collapsed configuration (non-inflated with an insertion fluid), catheter member 14 may be inserted into the body cavity 28. Upon inflation of a fluid medium into a fluid passageway between the balloon inner wall 26 and the balloon outer wall 24, double wall balloon 12 expands in radial direction 32 to diameter greater than the opening to the body cavity for retention of double wall balloon 12 within body cavity 28 as will be detailed in following paragraphs.

Initially, double wall balloon catheter system 10 (also referred to as catheter system 10) is inserted into a bladder cavity 28 with double wall balloon 12 being in a collapsed manner adjacent to a catheter outer surface 38 and upon placement in the radial direction 32, provides for inner balloon region 40 which is in fluid communication with catheter lumen 34. Catheter 14 includes one or more side-wall catheter orifices 42 to permit drainage of unwanted bodily fluid into catheter lumen 34 which is passed through double wall balloon orifices 22 into balloon inner region 40 and then external from balloon inner region 40 into catheter lumen 34. Side-wall orifices 42 are located within a coverage area of double wall balloon 12 on catheter member 14 in a manner to allow all side-wall orifices 44 to be in fluid communication with inner balloon cavity 40.

Unwanted bladder cavity fluids are then passed from bladder cavity 28 through double wall balloon orifice 22 into balloon inner region 40 and passed through side wall catheter orifices 42 into catheter lumen 34 for dispensing of the unwanted fluid external to catheter system 10.

An inflation fluid medium conduit 46 as shown in FIGS. 1 and 2 provide a passageway for fluid medium to be inserted into inflation passageway 48 between double wall balloon inner wall 26 and double wall balloon outer wall 24. Double wall balloon outer wall 24 and double wall balloon inner wall 26 form a substantially annular contour (in the embodiment schematically represented in FIG. 1) and as inflation medium is inserted into inflation passageway 48, both double wall balloon outer wall 24 and double wall balloon inner wall 26 are expanded to block the removal of catheter 14 from bladder cavity 28. The fluid medium may be a sterile fluid, air or other gas to be inserted into inflation passageway 48 under pressure to allow the radial expansion of the double wall balloon 12. As the inflation fluid medium flows within inflation passageway 48, such is routed around double wall balloon orifice 22 as is seen by directional arrow 50 to permit continuous flow of inflation fluid medium in a continuous manner throughout inflation passageway 48.

A plurality of flexible ties 52 may extend from the double wall balloon inner wall 26 to the double wall balloon outer wall 24 in a radial manner to permit maintaining the contour of the inflation passageway 48 during expansion in radial direction 32. Flexible ties 52 have sufficient flexibility to permit collapsibility when it is desired to remove catheter 14 from the bladder cavity.

Thus, in operation, inflation medium is inserted into inflation fluid medium conduit 46 for flow into inflation passageway 48 where the flow of the inflation fluid medium passes around each of the double wall balloon orifices 22 to continue in the pathway developed by the annular space provided by double wall balloon outer wall 24 and double wall balloon inner wall 26 for retention purposes of catheter 14. Once inserted into bladder cavity 28, drainage is provided by double wall balloon catheter system 10 to permit unwanted fluid to be drained from bladder cavity 28 through double wall balloon orifices 22 into balloon inner region 40 and then passage through side-wall catheter orifices 42 into catheter lumen 34 for dispensing of the draining fluid.

In order to maintain inflation fluid to predetermined levels of pressure and avoid fluid medium pressures which would be deleterious, a pressure monitor 54 may be provided in fluid communication with fluid medium conduit 46 for maintaining the pressure of the fluid medium being inserted into inflation passageway 48 for the minimization of possible over-inflation. Pressure monitors 54 are well known in the art and will not be further discussed. Pressure monitor or pressure gauge 54 is generally inserted into a pathway of the fluid medium within the medium conduit 56 at a location positioned at a location before the fluid medium conduit entrance which is schematically shown in FIG. 1.

In summary, double wall balloon catheter system 10 is essentially composed of (a) a hollow tube catheter member 14 defining a proximal end section, a distal end or tip section, and a balloon coverage section, and a proximal end section which is seen to be the section between the bladder wall 30 and the proximal end of the catheter member 14 with this section sometimes referred to as the urethral segment, (b) a double walled balloon having an inner balloon wall 26 and an outer balloon wall 24 which is secured to side-wall 14 of catheter member 14 and covers the balloon coverage section of the catheter member 14.

Tip distal end section 18 has an arcuate shape having a relatively large radius of curvature which results in a blunted end tip section 18. The blunted tip section curvature is of importance due to the fact that the tip section 18 may extend from the external surface of balloon outer wall by a minimal distance. The blunted contour of tip end section 18 reduces the possibility of catheter member 14 traumatizing the patients body tissue when the catheter member 14 abuts against the bodily tissue which in the case of double wall balloon catheter system 10 being inserted into a patient's bladder, would be the bladder wall 30.

Since drainage of unwanted body fluid is through the wall of catheter member 14 within the expanse covered by the inner and outer walls 26 and 24, there is no necessity of an extended tip section 18 having a plurality of orifices formed through the tip section 18 to accommodate numerous drainage orifices. Thus, as is shown in FIGS. 1 and 2, although catheter member 14 may include one (or a few) draining orifice 20 to aid in removal of unwanted body fluid, such is not a necessity and the tip end section 18 can be formed devoid of any orifice extending through the catheter end section tip 18. The highly blunted arcuate tip section 18 is advantageous over the known prior art which need an extended tip section since drainage orifices are generally formed in prior art tip sections necessitating a larger surface area to permit more draining orifices.

The double wall balloon catheter system 10 has two separate cavities, namely an enclosed passageway 48 which may be filled with an aqueous sterile solution for expansion of the inner/outer walls 24 and 26 to create retention of the double wall balloon catheter system 10 within the body cavity wall 30 while at the same time in open fluid communication with the body cavity 28 for drainage of the unwanted bodily fluids. The distal tip section 18, which is at the distal end of the catheter 14, remains within the body cavity and is generally formed of a rubber silicon, latex composition or like composition which is bio-compatible.

It is to be noted that the tip section 18 at the distal end of catheter 14 may include one or more openings or orifices 20 for draining body fluids, such as urine, from the body cavity or in the alternative, catheter tip section or distal end 18 may not have an opening and drainage is only provided through the fluid communication through the double wall balloon orifices 22, the balloon inner region 40, catheter drainage orifices 42.

Inner and outer walls 26 and 24 may be formed of a material which do not stretch or shrink that are secured to each other by threads or bands 52 that do not stretch and maintain a closed liquid filled passageway 48 between the two layers or walls 24 and 26 forming a spherical or oval shaped balloon structure when the liquid or pressurized gas is inserted into passageway 48 through inflation fluid medium conduit 46.

Referring now to FIG. 2, there is shown an embodiment of double wall balloon catheter system 10'. In this embodiment, balloon inner wall 26' is seen as a series of arcuate contours having cusp ends 56 which are adhered to balloon outer wall 24. Adherence can be made through use of an epoxy adhesive or some like material. Inflation fluid is passed into catheter 14 and flows through inflation fluid medium conduit 46 into fluid passageway 48' and passes around double wall balloon orifice 22 to permit a flow through inflation passageway 48' as is seen.

In this manner, when liquid or gas medium is introduced into inflation fluid medium conduit 46, such passes through inflation passageway 48' circumferentially between balloon inner wall 26 and balloon outer wall 24. Unwanted fluid is drained through balloon drain orifice 22 into balloon inner region 40' and then transmitted through one or more catheter orifices 42 as is seen by the directional arrow 44. Unwanted draining fluid enters catheter lumen 34 for passage external to double wall balloon catheter system 10.

In like manner to the embodiments shown in FIG. 1, inflation fluid medium conduit 46 may be connected to a pressure monitor or gauge system such as the pressure or gauge system depicted in FIG. 54 for controlling/monitoring the pressure of fluid contained within inflation passageway 48'. With this embodiment the flexible ties 52 provided in the embodiment shown in FIG. 1 are not needed.

Referring now to FIGS. 3 and 3A, there is shown double wall catheter system 10' directed to a double wall catheter system 10" which is particularly directed to a use of catheter system 10" for both restraining catheter 14 within the bladder cavity 28 and shown as first section 56 and a second section 58 where fluid section 56 provides for the double wall balloon 12' having an outer balloon wall 24' and an inner balloon wall 26' operationally activated in the same manner as that shown in FIGS. 1-2. With relation to system fluid section 56, there is provided an extended inflation fluid medium conduit 60 which passes in a longitudinal direction through system second section 58 below the bladder wall 30 where fluid medium is inserted into passageway 48" for passage between inner and outer walls 24" and 26" in an annular contouring. As is the case in the embodiment shown in FIGS. 1-2, unwanted bladder cavity fluid passes through double wall balloon orifices 22" for insertion into balloon inner region 40' which is in fluid communication with catheter lumen 34' by way of side-wall catheter orifices 42' for passage in longitudinal direction 16 external to double wall catheter system 10". In this embodiment inflation fluid medium conduit 46' is extended through system second section 58 for insertion into passageway 48" in operational concept similar to that provided in the embodiment shown in FIGS. 1-2 . Catheter 14 includes the catheter tip 18 having a drain or orifice 20 for passage therethrough of further drainage of the unwanted bodily fluid contained within bladder cavity 28. As is seen in the enlarged system section 58 the catheter 14 passes through the urethra and is situated adjacent the prostate 62. The second system section includes a second inflation medium conduit 64 which extends in longitudinal direction 16 for passage of inflation fluid medium into prostate passageway 66 to be routed around prostate balloon orifice 68 in a direction as indicated by the directional arrow 70. In this manner, inflation fluid radially extends prostate outer balloon wall 72 and inner prostate balloon wall 74 to be adjacent to or contiguous with prostate inner wall 76. Medicant conduit 78 extends through catheter 14 side-wall and is inserted into prostate inner region 80 which in itself is in fluid communication with prostate inner region 82 for insertion of medicant therein or thereon.

Thus, as is seen in this embodiment, double wall balloon catheter system 10" includes three conduits to provide inflation of the secondary balloon 84 by way of the pressurized inflation fluid in prostate passageway 66 as well as for a medicant conduit for insertion of the medicant into the prostate balloon inner region 80 and a secondary inflation conduit 64 for expansion of the secondary balloon 84. In this manner, unwanted bodily fluid is drained from the bladder cavity 28, medicant is inserted into the prostate 62 after expansion of the balloon inner and outer walls 72 and 74.

The above provides for containment of the double wall balloon catheter system 10" in relatively stable location with respect to the bladder and the prostate with the simultaneous drainage and medicant receiving of the prostate 62.

As an example, fabrication of double wall balloon catheter system 10', liquid rubber silicone may be poured into a vulcanization rubber mold in the shape of catheter 14 with a plurality of conduit openings formed on a proximal end of catheter 14 and one opening 20 formed through distal tip 18. The silicone may be heat cured for a selected amount of time and as subsequent to cooling catheter 14 is removed from the mold. As an alternative, a drain hole 20 may be punched through catheter 14 side wall 36 in the area of the distal tip 18 of the catheter 14 subsequent to the catheter 14 being cooled.

A band of thin cured latex is applied over the surface of the catheter 14 forming a sheath around catheter 14 in order that the thin band of latex covers the catheter openings. One or more holes 42 may be formed through the catheter wall 36 within the area covered by the thin band of cured latex which forms the inner wall 26'. The balloon inner wall 26' is inflated through the proximal main ports 42 by insertion of water through a syringe or other some-like technique entering the balloon inner region 40' through the balloon segment holes 42.

An adhesive material such as an adhesive epoxy such as latex are positioned on the outer surface of the inner balloon wall 26'. Inflation medium conduit 46' within the catheter side wall 36 to a space created between the inner and outer walls 26' and 24'.

Subsequently, the catheter balloon segment area is covered with a second coat (forming the balloon outer wall 24) with latex creating an enclosed space between the inner/outer layers or walls of the balloon which are tethered each to the other by the adhesive materials along the circumference of the surface of the balloon outer wall 24'. This provides for the adhesive 56 to now provide adhesive points which allows for an inflation passageway 48' and the inner/outer layers or inner/outer balloon wall members 26'/24' are tethered by the adhesive materials throughout the entire circumference of the double balloon walls 26' and 24.

The main conduit for catheter lumen 34' is deflated and water is removed from the catheter lumen 34 with a proximal port open to the environment. Two or more holes are punched or otherwise provided in the layers or walls 24' and 26' which are sealed from the enclosed space 48' between the inner and outer balloon walls 24' and 26' and in fluid communication with the body cavity fluids and the catheter side wall orifices 42'.

Water is inserted into inflation conduit 46' between the inner/outer balloon walls 24' and 26'. The balloon walls 24'/26' are then deflated by withdrawing water from the inflation conduit 46' and the walls 26'/24' collapse over the outer surface of the catheter 14. Two spaces or volumes are formed within the balloon namely balloon inner regions 40' where there is an enclosed outer volume 48' connected to the inflation fluid medium conduit 46'. An inner open space is created within the inflated balloon and is connected to an inner open space 40' is in fluid communication with catheter lumen 34 and a fluid flow path is created from balloon drain orifice 22' through catheter side wall orifice 42' into catheter lumen 34'. In this manner a pathway is provided from the body cavity 28 in a continuous manner through the openings or orifices 22' and then through the orifices 42' into the catheter lumen 34' for expelling to the environment. In this manner a double wall balloon catheter system 10' can be fabricated.

Although aspects of the present disclosure have been described in connection with specific forms and embodiments thereof, it will be appreciated that various modifications other than those discussed above may be resorted to without departing from the spirit or scope of the present disclosure as defined in the appended claims. For example, functionally equivalent elements may be substituted for those specifically shown and described, certain features may be used independently of other features, and in certain cases, particular locations of the elements may be reversed or interposed, all without departing from the spirit or scope of the present disclosure as defined in the appended claims.

What is claimed is:

1. A double wall catheter system adapted to be retained within a patient body cavity and drain bodily fluid from the patient body cavity comprising:

(a) a catheter member extending in a longitudinal direction having a catheter lumen, said catheter member defining a catheter sidewall member extending in a longitudinal direction, said catheter member having at least one catheter drainage orifice formed through said catheter sidewall member adapted for draining a body cavity drainage fluid to pass therethrough;

(b) a balloon coupled to said catheter sidewall member, said balloon having a double balloon wall configuration defining an inner balloon wall and an outer balloon wall forming in cross-section a balloon fluid passageway therebetween;

(c) a balloon fluid inflation conduit extending within said catheter sidewall member in fluid communication with said balloon fluid passageway for expansion of said balloon in a radial direction with respect to said longitudinal direction for retention of said catheter member within said patient body cavity when an inflation fluid is inserted into said balloon fluid passageway and, (d) at least one balloon through conduit formed between and joined to said inner balloon wall and said outer balloon wall in fluid communication with said patient's body cavity and an inner balloon cavity, said inner balloon cavity being in fluid communication with said at least one catheter drainage orifice for passage of fluid from said patient body cavity into said catheter lumen.

2. The double wall catheter system as recited in claim 1 where said balloon fluid passageway is annular in cross-section throughout a circumference of said balloon.

3. The double wall catheter system as recited in claim 2 wherein said inner balloon wall and said outer balloon wall are formed of a substantially flexible and inelastic composition.

4. The double wall catheter system as recited in claim 2 wherein said at least one catheter drainage orifice is formed at a tip section of said catheter member located at a distal end of said catheter sidewall member.

5. The double wall catheter system as recited in claim 2 wherein said tip section of said catheter member is arcuately formed and in one-piece formation with said catheter member sidewall.

6. The double wall catheter system as recited in claim 5 wherein said tip section of said catheter member is devoid of a tip section body fluid drainage orifice.

7. The double wall catheter system as recited in claim 2 wherein said at least one catheter drainage orifice is formed through said catheter sidewall member in fluid communication with said inner balloon cavity.

8. The double wall catheter system as recited in claim 7 wherein said balloon member is secured to said catheter sidewall member and covers said at least one catheter drain orifice formed in said catheter sidewall member.

9. The double wall catheter system as recited in claim 2 wherein said inner balloon wall and said outer balloon wall are formed in one-piece formation.

10. The double wall catheter system as recited in claim 2 wherein said at least one balloon through conduit is secured to said inner balloon wall and said outer balloon wall in fluid tight securement each to the other to permit said body cavity drainage fluid to pass through said at least one balloon through conduit from said patient body cavity to said inner balloon cavity.

11. The double wall catheter system as recited in claim 2 wherein said inner balloon wall and said outer balloon wall are tethered each to the other by a plurality of balloon tether members secured on opposing ends thereof to said inner and outer balloon walls respectively.

12. The double wall catheter system as recited in claim 11 wherein said plurality of balloon tether members are substantially spaced equidistant from each other within said balloon fluid passageway, said plurality of balloon tether members being flexible and substantially inelastic.

13. The double wall catheter system as recited in claim 12 wherein each of said tether members are thread elements or band elements for structurally maintaining a substantially equidistant distance from said inner balloon wall and said outer balloon wall when said fluid passageway is pressurized by said insertion fluid.

14. The double wall catheter system as recited in claim 1 wherein said patient body cavity is formed internal to a bladder of said patient.

15. The double wall catheter system as recited in claim 1 wherein said inner balloon wall and said outer balloon wall are formed of a substantially flexible and inelastic biocompatible composition.

* * * * *